(12) United States Patent
Schilter

(10) Patent No.: US 9,050,151 B2
(45) Date of Patent: Jun. 9, 2015

(54) BONE PLATE AND AIMING BLOCK

(71) Applicant: Stryker Trauma SA, Selzach (CH)

(72) Inventor: Arlette Schilter, Feldbrunnen (CH)

(73) Assignee: Stryker Trauma SA (CH)

( * ) Notice: Subject to any disclaimer, the term of this patent is extended or adjusted under 35 U.S.C. 154(b) by 95 days.

(21) Appl. No.: 13/785,121

(22) Filed: Mar. 5, 2013

(65) Prior Publication Data

US 2013/0238032 A1 Sep. 12, 2013

Related U.S. Application Data

(60) Provisional application No. 61/607,242, filed on Mar. 6, 2012.

(51) Int. Cl.
*A61B 17/80* (2006.01)
*A61B 17/84* (2006.01)
*A61B 17/17* (2006.01)

(52) U.S. Cl.
CPC .............. *A61B 17/80* (2013.01); *A61B 17/846* (2013.01); *A61B 17/1728* (2013.01)

(58) Field of Classification Search
CPC .... A61B 17/17; A61B 17/1728; A61B 17/80; A61B 17/8052; A61B 17/8057
USPC ..................... 606/70, 71, 86 B, 96, 280–299
See application file for complete search history.

(56) References Cited

U.S. PATENT DOCUMENTS

| | | |
|---|---|---|
| 2,494,229 A | 1/1950 | Collison |
| 2,935,905 A | 5/1960 | Winslow |
| 4,788,970 A | 12/1988 | Karas et al. |
| 5,147,367 A | 9/1992 | Ellis |
| 5,417,694 A | 5/1995 | Marik et al. |
| 5,423,826 A | 6/1995 | Coates et al. |
| 5,507,801 A | 4/1996 | Gisin et al. |
| 5,851,207 A | 12/1998 | Cesarone |
| 5,897,557 A | 4/1999 | Chin et al. |
| 5,935,128 A | 8/1999 | Carter et al. |
| 5,993,449 A | 11/1999 | Schlapfer et al. |
| 6,007,535 A | 12/1999 | Rayhack et al. |

(Continued)

FOREIGN PATENT DOCUMENTS

| | | |
|---|---|---|
| EP | 0 993 275 A1 | 4/2000 |
| JP | 2009178543 A | 8/2009 |

(Continued)

OTHER PUBLICATIONS

Partial European Search Report, EP 07 02 4429.

*Primary Examiner* — Christian Sevilla
*Assistant Examiner* — Eric S Gibson
(74) *Attorney, Agent, or Firm* — Lerner, David, Littenberg, Krumholz & Mentlik, LLP

(57) ABSTRACT

A bone-fixation system is disclosed, the system comprising a bone plate having a section with a plurality of holes and a recessed area at least partially surrounding one or more of the holes, the recessed area defining a floor surface situated below a top surface of the plate, the floor surface extending at least partially between some or all of the plurality of holes, and an aiming device having a plurality of holes arranged to align with the plurality of holes in the plate and an extension, the extension being receivable within the recessed area and defining a bottom surface adapted to at least partially rest on the floor surface.

22 Claims, 7 Drawing Sheets

(56) References Cited

U.S. PATENT DOCUMENTS

| | | |
|---|---|---|
| 6,235,034 B1 * | 5/2001 | Bray .................. 606/71 |
| 6,342,057 B1 | 1/2002 | Brace et al. |
| 6,358,250 B1 | 3/2002 | Orbay |
| 6,364,882 B1 | 4/2002 | Orbay |
| 6,379,364 B1 | 4/2002 | Brace et al. |
| 6,440,135 B2 | 8/2002 | Orbay et al. |
| 6,692,503 B2 | 2/2004 | Foley et al. |
| 6,706,046 B2 | 3/2004 | Orbay et al. |
| 6,755,831 B2 | 6/2004 | Putnam et al. |
| RE38,684 E | 1/2005 | Cesarone |
| 6,866,665 B2 | 3/2005 | Orbay |
| 6,926,720 B2 | 8/2005 | Castaneda |
| 7,081,119 B2 | 7/2006 | Stihl |
| 7,153,309 B2 | 12/2006 | Huebner et al. |
| 7,250,053 B2 | 7/2007 | Orbay |
| 7,282,053 B2 | 10/2007 | Orbay |
| 7,294,130 B2 | 11/2007 | Orbay |
| 7,578,825 B2 * | 8/2009 | Huebner .................. 606/104 |
| 7,625,378 B2 | 12/2009 | Foley |
| 7,648,508 B2 | 1/2010 | Lutz et al. |
| 7,731,721 B2 | 6/2010 | Rathbun et al. |
| 7,736,380 B2 | 6/2010 | Johnston et al. |
| 7,740,634 B2 | 6/2010 | Orbay et al. |
| 7,771,433 B2 | 8/2010 | Orbay et al. |
| 7,909,848 B2 | 3/2011 | Patel et al. |
| 7,935,123 B2 | 5/2011 | Fanger et al. |
| 7,935,126 B2 | 5/2011 | Orbay et al. |
| 8,029,551 B2 * | 10/2011 | Running et al. .............. 606/295 |
| 8,052,729 B2 * | 11/2011 | Dube .................. 606/289 |
| 8,100,952 B2 | 1/2012 | Matityahu |
| 8,162,950 B2 * | 4/2012 | Digeser et al. .................. 606/96 |
| 8,231,625 B2 * | 7/2012 | Graham et al. .................. 606/71 |
| 8,523,862 B2 * | 9/2013 | Murashko, Jr. .................. 606/71 |
| 8,523,919 B2 * | 9/2013 | Huebner et al. .............. 606/280 |
| 8,641,741 B2 * | 2/2014 | Murashko, Jr. .............. 606/280 |
| 8,652,180 B2 * | 2/2014 | Federspiel et al. ............ 606/281 |
| 2003/0040748 A1 | 2/2003 | Aikins et al. |
| 2003/0153918 A1 | 8/2003 | Putnam et al. |
| 2004/0102788 A1 | 5/2004 | Huebner et al. |
| 2004/0204716 A1 | 10/2004 | Fanger et al. |
| 2004/0204717 A1 | 10/2004 | Fanger et al. |
| 2005/0015092 A1 | 1/2005 | Rathbun et al. |
| 2005/0015093 A1 | 1/2005 | Suh et al. |
| 2005/0049594 A1 | 3/2005 | Wack et al. |
| 2005/0085818 A1 * | 4/2005 | Huebner .................. 606/69 |
| 2005/0137606 A1 | 6/2005 | Binder et al. |
| 2005/0159747 A1 * | 7/2005 | Orbay .................. 606/69 |
| 2005/0228398 A1 | 10/2005 | Rathbun et al. |
| 2005/0234458 A1 | 10/2005 | Huebner |
| 2005/0234472 A1 | 10/2005 | Huebner |
| 2006/0095044 A1 | 5/2006 | Grady et al. |
| 2006/0100637 A1 | 5/2006 | Rathbun et al. |
| 2006/0116679 A1 | 6/2006 | Lutz et al. |
| 2006/0149257 A1 | 7/2006 | Orbay et al. |
| 2006/0161158 A1 | 7/2006 | Orbay et al. |
| 2006/0161168 A1 | 7/2006 | Matthys |
| 2006/0173458 A1 | 8/2006 | Forstein et al. |
| 2006/0189996 A1 | 8/2006 | Orbay et al. |
| 2006/0200157 A1 | 9/2006 | Orbay et al. |
| 2006/0229618 A1 * | 10/2006 | Dube .................. 606/69 |
| 2007/0167953 A1 * | 7/2007 | Prien et al. .................. 606/102 |
| 2007/0173836 A1 | 7/2007 | Prien |
| 2007/0173839 A1 * | 7/2007 | Running et al. .................. 606/69 |
| 2007/0173843 A1 | 7/2007 | Matityahu |
| 2007/0191855 A1 | 8/2007 | Orbay et al. |
| 2008/0183172 A1 | 7/2008 | Fritzinger |
| 2009/0088768 A1 * | 4/2009 | Grant et al. .................. 606/102 |
| 2009/0157086 A1 | 6/2009 | Digeser et al. |
| 2009/0228047 A1 * | 9/2009 | Derouet et al. .............. 606/286 |
| 2009/0312760 A1 | 12/2009 | Forstein et al. |
| 2010/0179599 A1 * | 7/2010 | Derouet et al. .............. 606/280 |
| 2010/0268283 A1 * | 10/2010 | Orbay .................. 606/281 |
| 2011/0106086 A1 * | 5/2011 | Laird .................. 606/70 |
| 2011/0172669 A1 | 7/2011 | Castaneda et al. |
| 2011/0313422 A1 | 12/2011 | Schwager et al. |
| 2012/0041447 A1 | 2/2012 | Schwer et al. |
| 2012/0078252 A1 * | 3/2012 | Huebner et al. .............. 606/70 |
| 2012/0078312 A1 * | 3/2012 | Federspiel et al. ............ 606/281 |
| 2012/0191104 A1 * | 7/2012 | Jost et al. .................. 606/102 |
| 2012/0253347 A1 * | 10/2012 | Murashko, Jr. .................. 606/71 |
| 2013/0238032 A1 * | 9/2013 | Schilter .................. 606/281 |

FOREIGN PATENT DOCUMENTS

| | | |
|---|---|---|
| WO | 01/82804 | 11/2001 |
| WO | 2005092225 A1 | 10/2005 |
| WO | 2006081483 A1 | 8/2006 |

* cited by examiner

BONE PLATE AND AIMING BLOCK

CROSS-REFERENCE TO RELATED APPLICATIONS

The present application claims the benefit of the filing date of U.S. Provisional Patent Application No. 61/607,242, filed Mar. 6, 2012 and entitled "Bone Plate and Aiming Block," the disclosure of which is hereby incorporated by reference herein.

BACKGROUND OF THE INVENTION

The present invention relates to bone plates, and more particularly, the insertion of screws through plates for the purpose of repairing fractures.

Bone plates are widely utilized in the repair of certain fractures of bones in both human and animal bodies. Generally, such plates are designed to be fixed on either side of a fracture in order to maintain the portions of the bone created by the fracture in registration with one another in order to promote healing of the bone. Typically, the plates are fixed via screws, pegs, or the like, which may be inserted at different angles in order to secure the best purchase of bone possible.

It is also widely known to utilize aiming or guiding blocks for guiding a drill and/or a screw during insertion so that the screw ultimately extends along a desired axis. Such guides take many different forms with the general goal being to extend the depth of a bone plate hole and provide stability to the drill and/or screw during the drilling and insertion processes. While generally suited for their intended purpose, these guides have some drawbacks. For instance, many require intricate attachment mechanisms that increase the difficulty of a surgery, while others suffer from misalignment either during attachment or even thereafter. Likewise, many require cumbersome instruments for use in initial placement of the aiming block on the bone plate, as well as overly complicated means for fixing the blocks with respect to the bone plates.

Therefore, there exists a need for an improved aiming or guide block for use in connection with bone plates.

BRIEF SUMMARY OF THE INVENTION

A first aspect of the present invention is a bone-fixation system including a bone plate having a recessed section with a plurality of first holes and an aiming block including an extension for reception within the recess and second holes that align with the first holes when the extension is received within the recess. Other embodiments of this first aspect may further include a joystick having a threaded distal end for reception within a first threaded hole of the plate and within a second threaded hole of the aiming block. Still further embodiments may allow the joystick to maintain the aiming block in position when the distal end is threaded into the first threaded hole of the bone plate.

A second aspect of the present invention is a bone-fixation system, the system comprising a bone plate having a section with a plurality of holes and a recessed area at least partially surrounding one or more of the holes, the recessed area defining a floor surface situated below a top surface of the plate, the floor surface extending at least partially between some or all of the plurality of holes. An aiming device also forms part of the system and has a plurality of holes arranged to align with the plurality of holes in the plate and an extension, the extension being receivable within the recessed area and defining a bottom surface adapted to at least partially rest on the floor surface. In some embodiments of this second aspect, the bone plate includes a head, and the recessed area extends along a major portion of the head.

A third aspect of the invention comprises a bone-fixation system including a bone plate having a section with a plurality of holes and a recessed area at least partially surrounding one or more of the holes, the recessed area defining a floor surface situated below a top surface of the plate, the floor surface extending at least partially between some or all of the plurality of holes. An aiming device also forms part of the system and has a plurality of holes arranged to align with the plurality of holes in the plate and an extension, the extension being receivable within the recessed area and defining a bottom surface adapted to at least partially rest on the floor surface. Lastly, an insertion tool is included in the system and comprises a handle and a shaft, a distal end of the insertion tool being engageable with the aiming device to manipulate the aiming device into engagement with the plate. In some cases, the insertion tool includes an extension projecting from the shaft and a shoulder, a diameter of the shoulder being greater than a diameter of the extension, the extension being insertable through at least one of the holes of the aiming device and into a hole in the plate so that the shoulder abuts a top surface of the aiming device.

A fourth aspect of the invention is a method of implanting a bone plate, the method comprising: (1) providing a bone plate having a section with a plurality of holes and a recessed area adjacent one or more of the holes; (2) providing an aiming device having a plurality of holes and an extension, at least some of the plurality of holes being alignable with the plurality of holes in the plate; (3) engaging a distal end of an insertion tool with at least one of the holes in the aiming device; (4) after the engaging step, manipulating the insertion tool to engage the aiming device with the plate, the extension of the aiming device being situated within the recessed area of the plate; and (5) engaging the distal end of the insertion tool with at least one hole in the plate so that a shoulder of the insertion tool engages a top surface of the aiming device to secure the aiming device to the plate. The engaging steps of the method may, in one embodiment, comprise rotating a threaded distal end of the insertion tool, such that the threaded distal end engages a threaded hole formed in the aiming device or the plate.

BRIEF DESCRIPTION OF THE DRAWINGS

A more complete appreciation of the subject matter of the present invention and the various advantages thereof can be realized by reference to the following detailed description, in which reference is made to the accompanying drawings in which.

DETAILED DESCRIPTION

Figure 1:
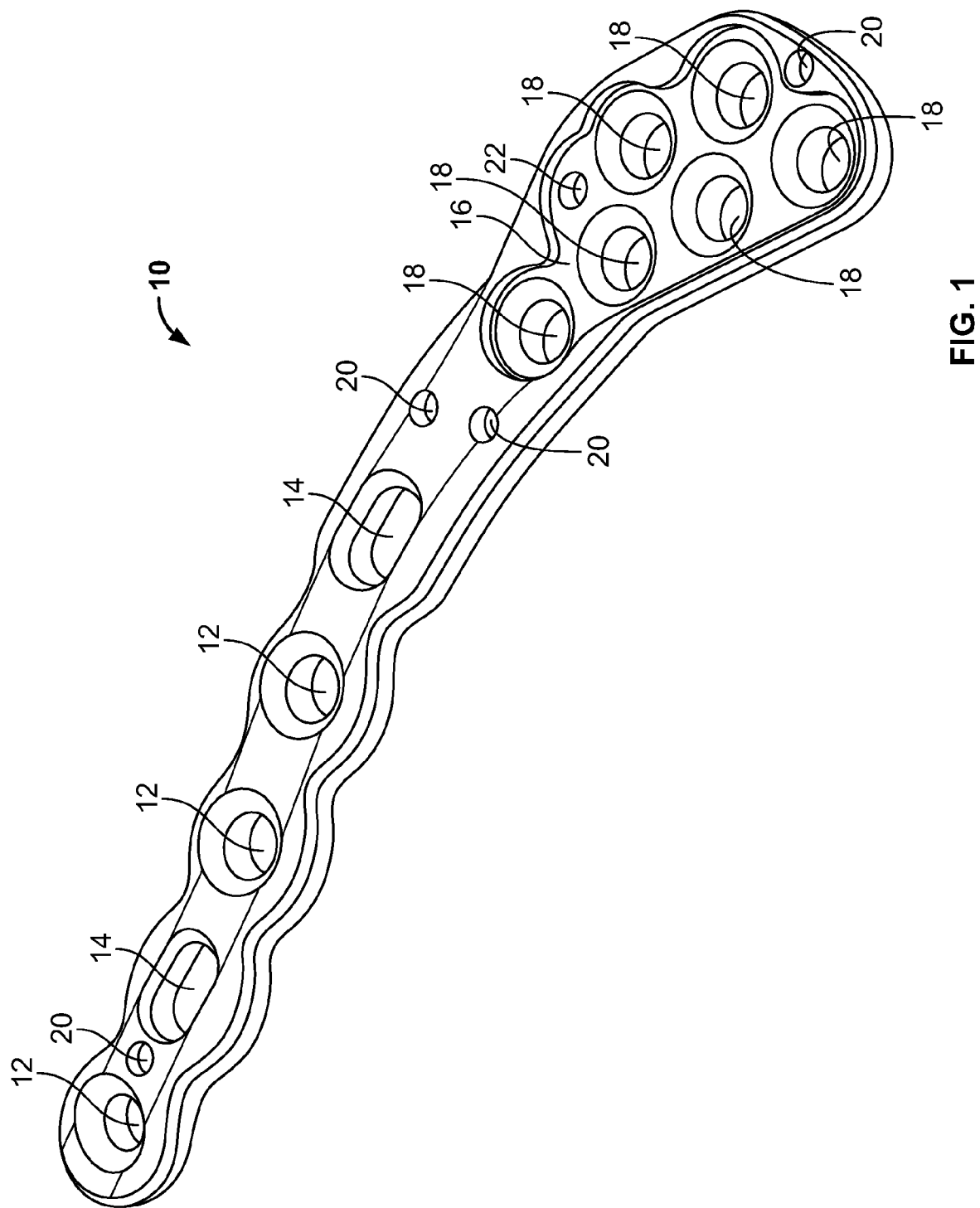
FIG. 1 is a top perspective view of a bone plate according to one embodiment of the present invention.

In describing the preferred embodiments of the invention (s) illustrated and to be described with respect to the drawings, specific terminology will be used for the sake of clarity. However, the invention(s) is not intended to be limited to any specific terms used herein, and it is to be understood that each specific term includes all technical equivalents, which operate in a similar manner to accomplish a similar purpose.

Referring to the drawings, wherein like reference numerals refer to like elements, FIGS. 1-10 depict components usable in fixation of human clavicle fractures. At the outset, it is to be understood that while the various components discussed herein are directed toward a use in connection with fractured clavicle bones, such components may be modified (if necessary) to have applicability in the repair of fractures in other bones in human or animal bodies. Those of ordinary skill in the art would readily recognize that such components, although discussed in connection with a single purpose, have applicability for other purposes in the orthopedic field.

Beginning with FIG. 1, there is shown a bone plate 10 configured for use in fixing a clavicle fracture. Bone plate 10 includes a plurality of bone screw receiving holes 12 that may facilitate the locking or fixation of such screws to plate 10 and the plate to the bone, elongate holes 14 that may facilitate the reduction of the fracture through the use of compression screws, a recessed area 16 including a plurality of bone screw receiving holes 18 similar to bone screw holes 12, a plurality of K-wire or suture receiving holes 20, and a threaded hole 22 situated within recessed area 16. Bone plate 10 is preferably constructed of a metallic material such as titanium or the like, and may be designed to be bendable in order to fit certain profiles of certain clavicle bones. In addition, it is noted that both holes 12 and 18 may be fitted with a rim capable of being deformed by the head of a bone screw, thereby fixing the bone screw to the plate when inserted. Holes 12, 14 and 18 can also be designed to receive different types of screws, for instance, any number of those holes can receive locking, non-locking or compression screws, as well as pins or other fixation mechanisms.

Figure 2A:
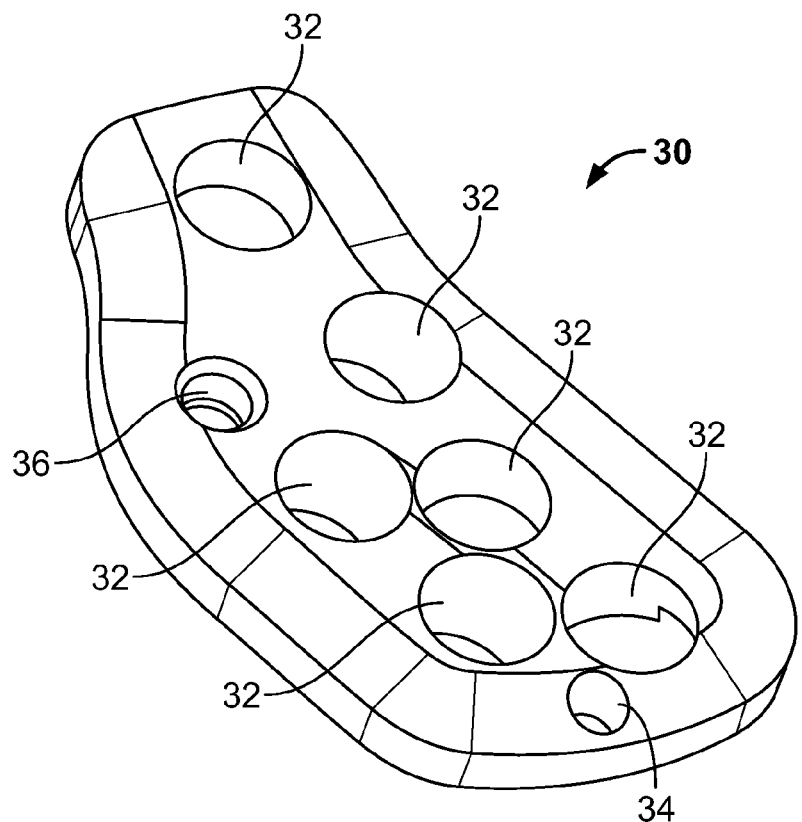
FIG. 2A is a top perspective view of a right-oriented aiming block for use with a bone plate according to the present invention.
Figure 2B:
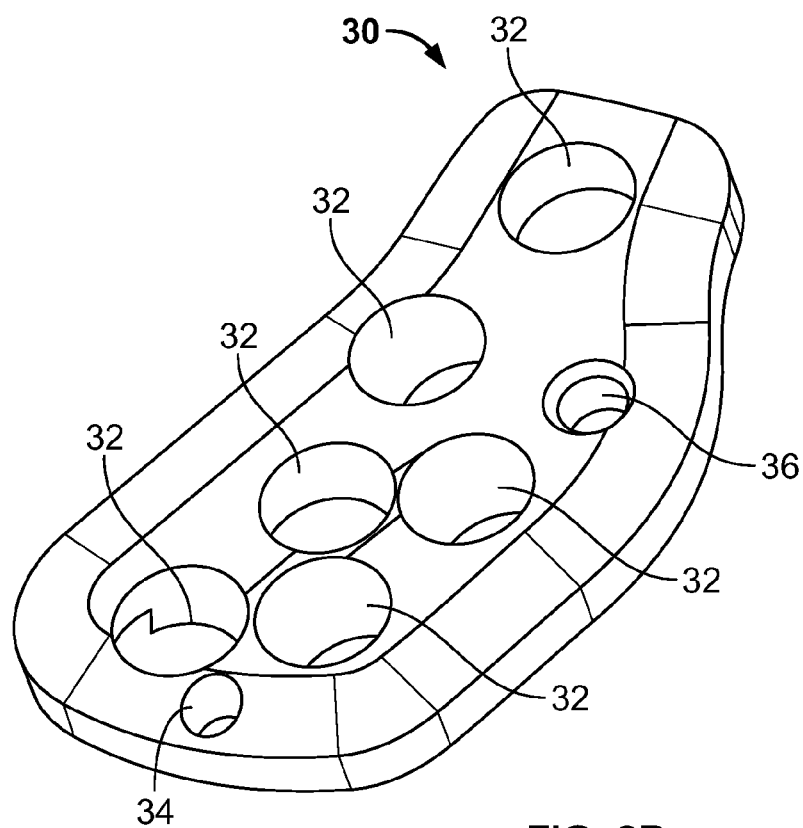
FIG. 2B is a top perspective view of a left-oriented aiming block for use in connection with the bone plate shown in FIG. 1.

FIGS. 2A and 2B depict aiming blocks 30, which include nearly identical structure, but which are configured for use with two different bone plates 10. For instance, while block 30 of FIG. 2B is configured to cooperate with recess 16 of plate 10, as shown in FIG. 1, block 30 of FIG. 2A exhibits an opposite construction suited for a plate oppositely constructed to the one shown in FIG. 1. In other words, where plate 10 may be for use with a clavicle on one side of the body, an oppositely configured plate would be utilized on the other side of the body. For the sake of simplicity, only a single aiming block 30 will be referred to herein. Preferably, block 30 is constructed of polymeric or metallic material, such as PEEK, titanium, or stainless steel, but it is to be understood that any suitable type of material may be employed.

Figure 3:
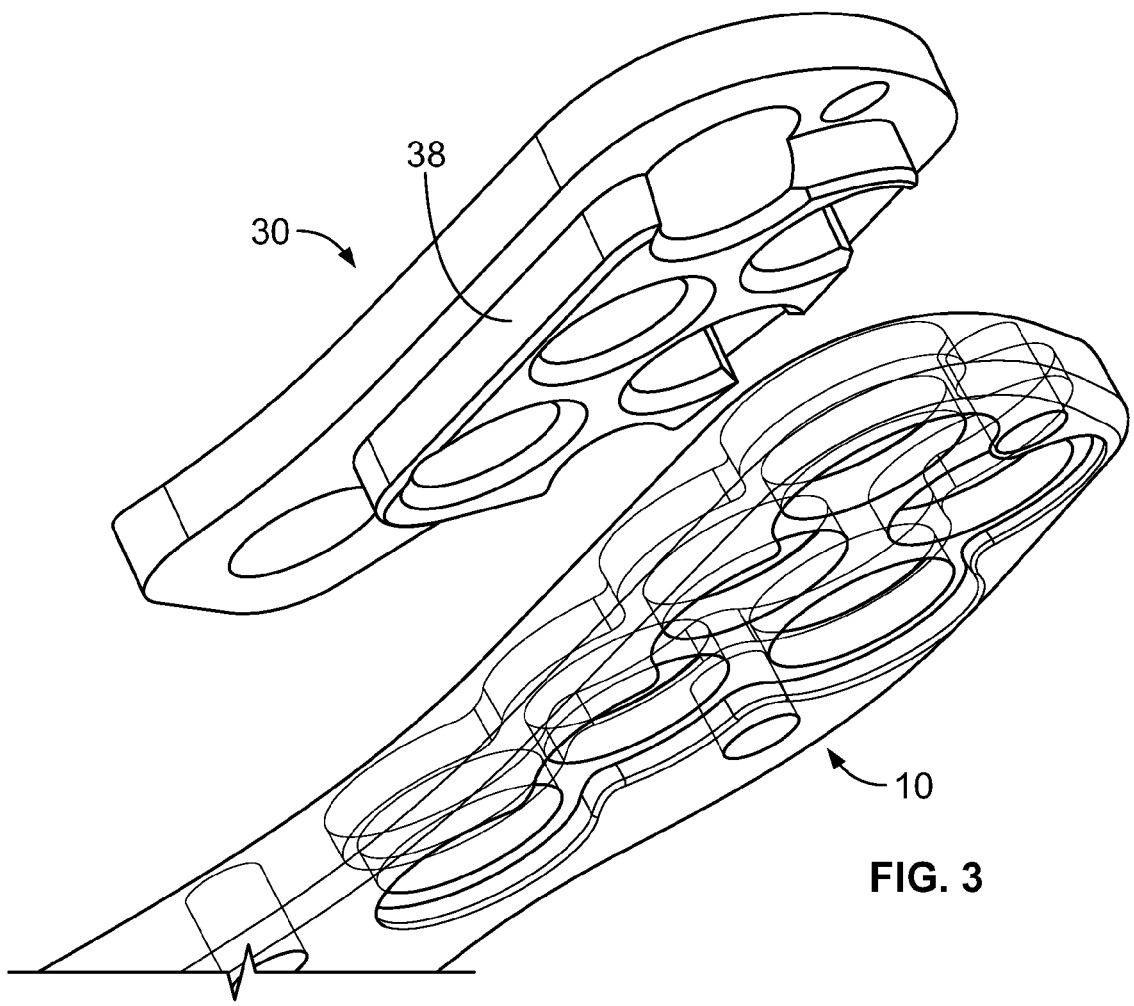
FIG. 3 is a bottom perspective view of the bone plate of FIG. 1 (shown as transparent) with the aiming block of FIG. 2B placed adjacent thereto.
Figure 4:
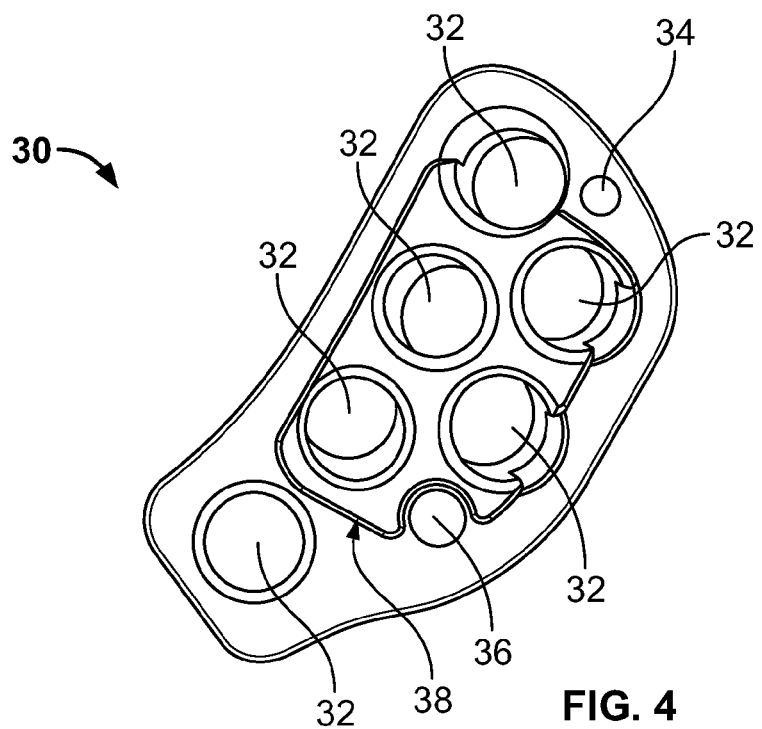
FIG. 4 is a bottom view of the aiming block of FIG. 2B.

Aiming block 30 includes holes 32 which are designed to align with holes 18 when aiming block 30 is placed within recess 16 of plate 10. Likewise, a K-wire hole 34 is provided on aiming block 30 to align with K-wire hole 20 of plate 10. Finally, a threaded hole 36 is provided on aiming block 30, which is aligned with threaded hole 22 located within recess 16 of plate 10. As is best shown in FIGS. 3 and 4, aiming block 30 also includes an extension 38 designed to cooperate and extend into recess 16 of plate 10. Extension 38 is preferably sized and shaped so as to fit snugly within recess 16 and prevent aiming block 30 from moving when engaged with plate 10. FIG. 4 best depicts the specific shape of extension 38, and it is particularly pointed out that the extension is a somewhat discontinuous structure by virtue of the hole structure of block 30. It is to be understood that extension 38 may be many shapes, as long as such cooperates with recess 16 to keep block 30 aligned with plate 10. Moreover, extension 38 could be sized so as to form an interference fit or taper lock with recess 16, or such could include a locking structure designed to cooperate with a locking structure in recess 16.

Figure 5:
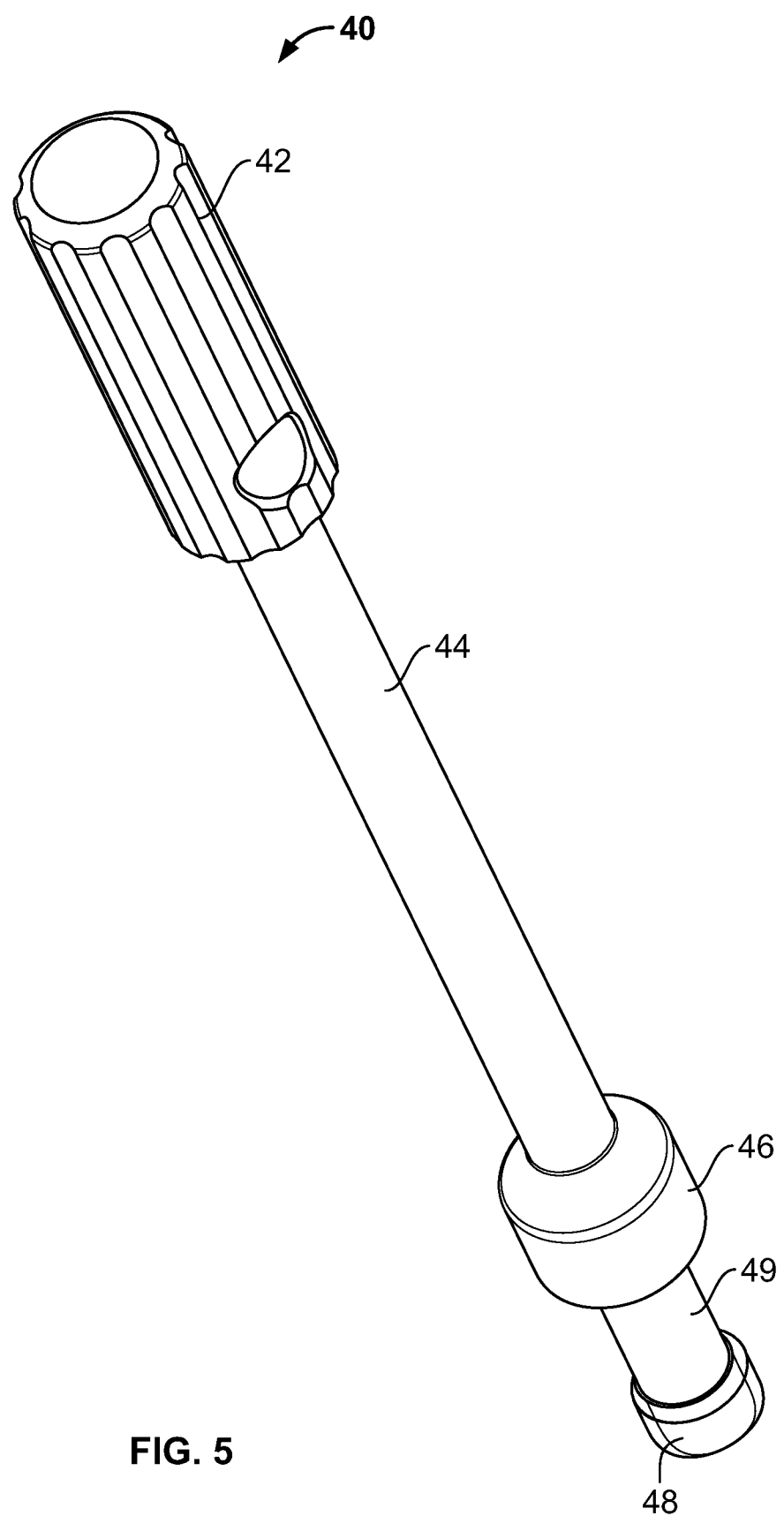
FIG. 5 is perspective view of a joystick for use in placement of the aiming blocks of the present invention.

FIG. 5 depicts joystick 40, which is a tool designed for cooperation with both aiming block 30 and plate 10. Joystick 40 includes a handle 42, an elongate shaft 44, a shoulder section 46, and a threaded distal tip 48. In addition, a section 49 extends between shoulder section 46 and distal tip 48, and includes a diameter that is less than the diameters of both of those flanking sections. As with the other components discussed in the present application, joystick 40 can be constructed of many different materials, including preferably metallic materials such as titanium or stainless steel. It is to be understood that while distal tip 48 is threaded in the preferred embodiment it can include any number of different fixation means, such as taper lock devices, friction fit devices, and ball detent structures.

Figure 6:
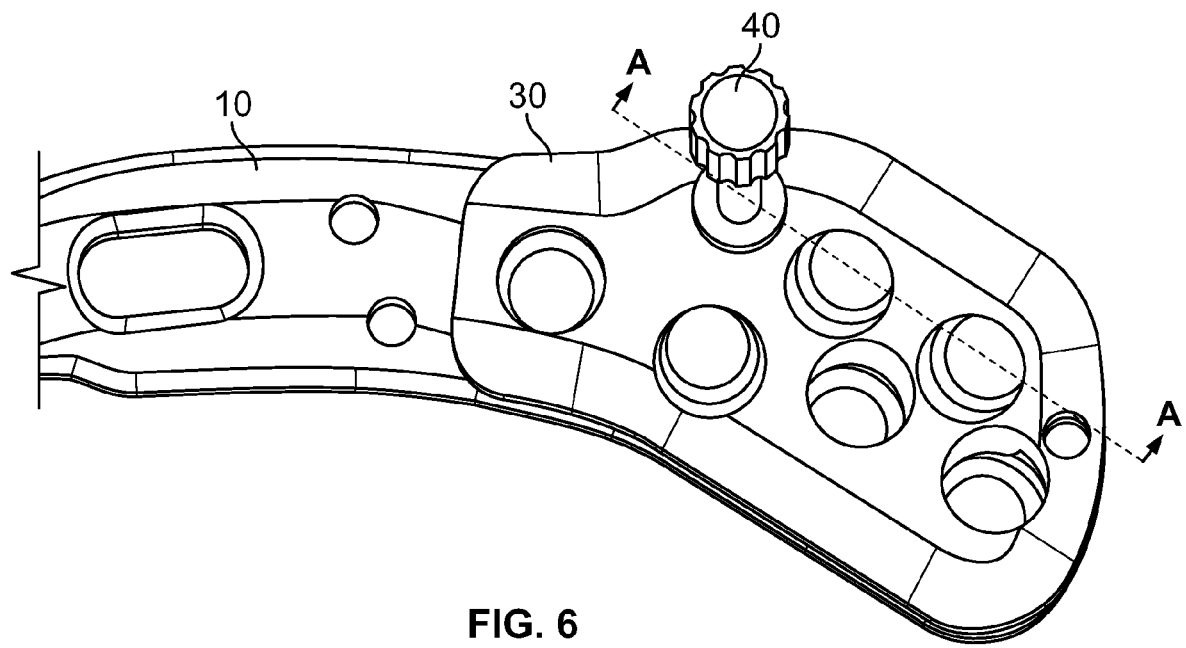
FIG. 6 is a top view of a construct consisting of the bone plate of FIG. 1, the aiming block of FIG. 2B, and the joystick of FIG. 5.
Figure 7:
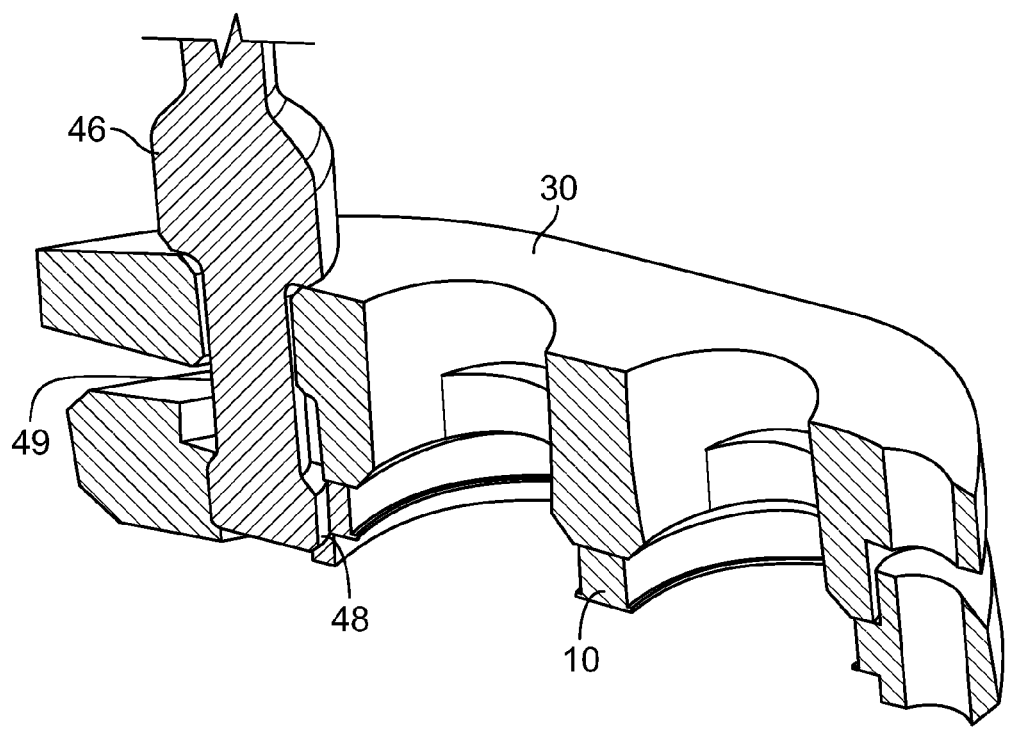
FIG. 7 is a cross-sectional view taken on line A-A of FIG. 6 depicting the cooperation among the bone plate, the aiming block, and the joystick.
Figure 9:
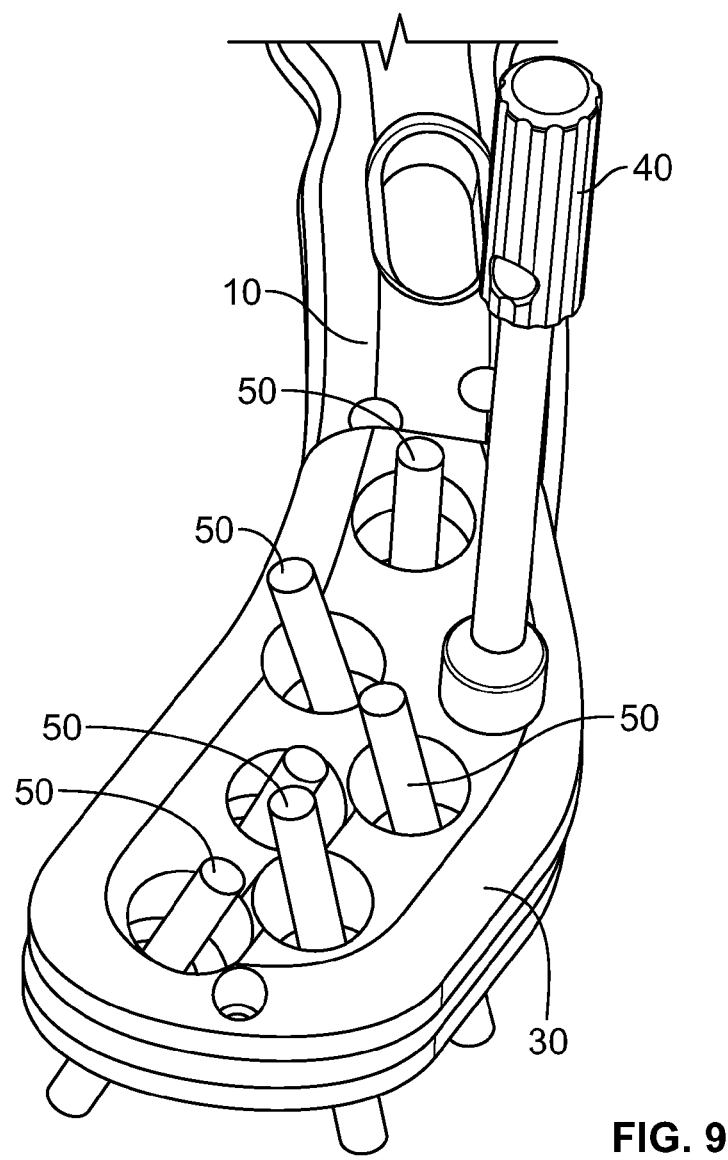
FIG. 9 is a perspective view of the bone plate, aiming block, and joystick construct with cylindrical bodies meant to represent screws, pegs, or other fixation members placed through the holes formed in the aiming block and bone plate.

In use, as is depicted in FIGS. 6, 7, and 9, joystick 40 is designed to thread into both hole 22 of plate 10 and hole 36 of aiming block 30. Specifically, during use, a surgeon first threads distal tip 48 into threaded hole 36 of aiming block 30. In this position, joystick 40 may be utilized to manipulate and move aiming block 30 into a position within the body and on plate 10, which is in turn placed on a bone. Once extension 38 of aiming block 30 is placed within recess 16 of plate 10, thereby ensuring proper placement of aiming block 30 on plate 10, additional threading of joystick 40, and in particular distal end 48, can occur. This results in the position best shown in the cross-sectional view of FIG. 7, where distal tip 48 is threaded into threaded plate hole 22, and shoulder section 46 abuts a top surface of aiming block 30 around hole 36. It is to be understood that the smaller diameter of section 49 (as well as its length) allows for joystick 40 to extend through threaded hole 36 of aiming block 30 and ultimately into the plate. In this position, aiming block 30 is pressed against plate 10 by virtue of the abutment of shoulder section 46 against the top surface of the plate, thereby essentially affixing the aiming block in place.

Figure 8:
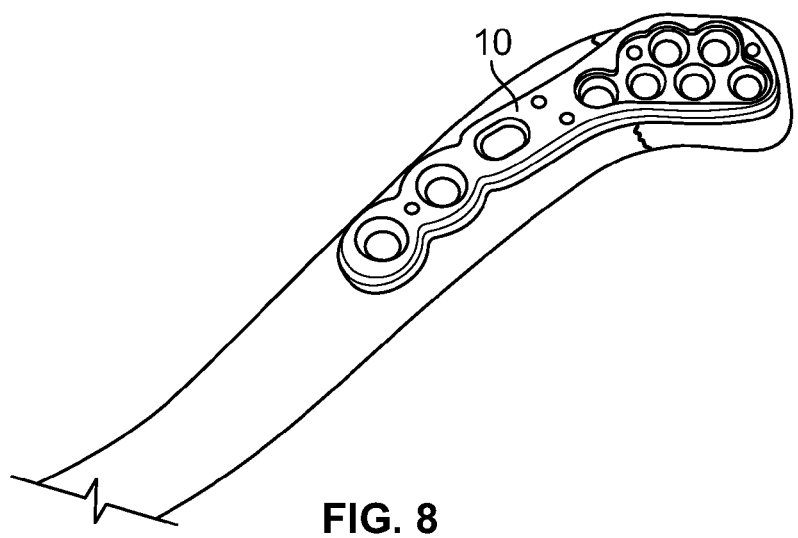
FIG. 8 is a perspective view of the bone plate of FIG. 1 shown placed on a fractured clavicle bone.
Figure 10:
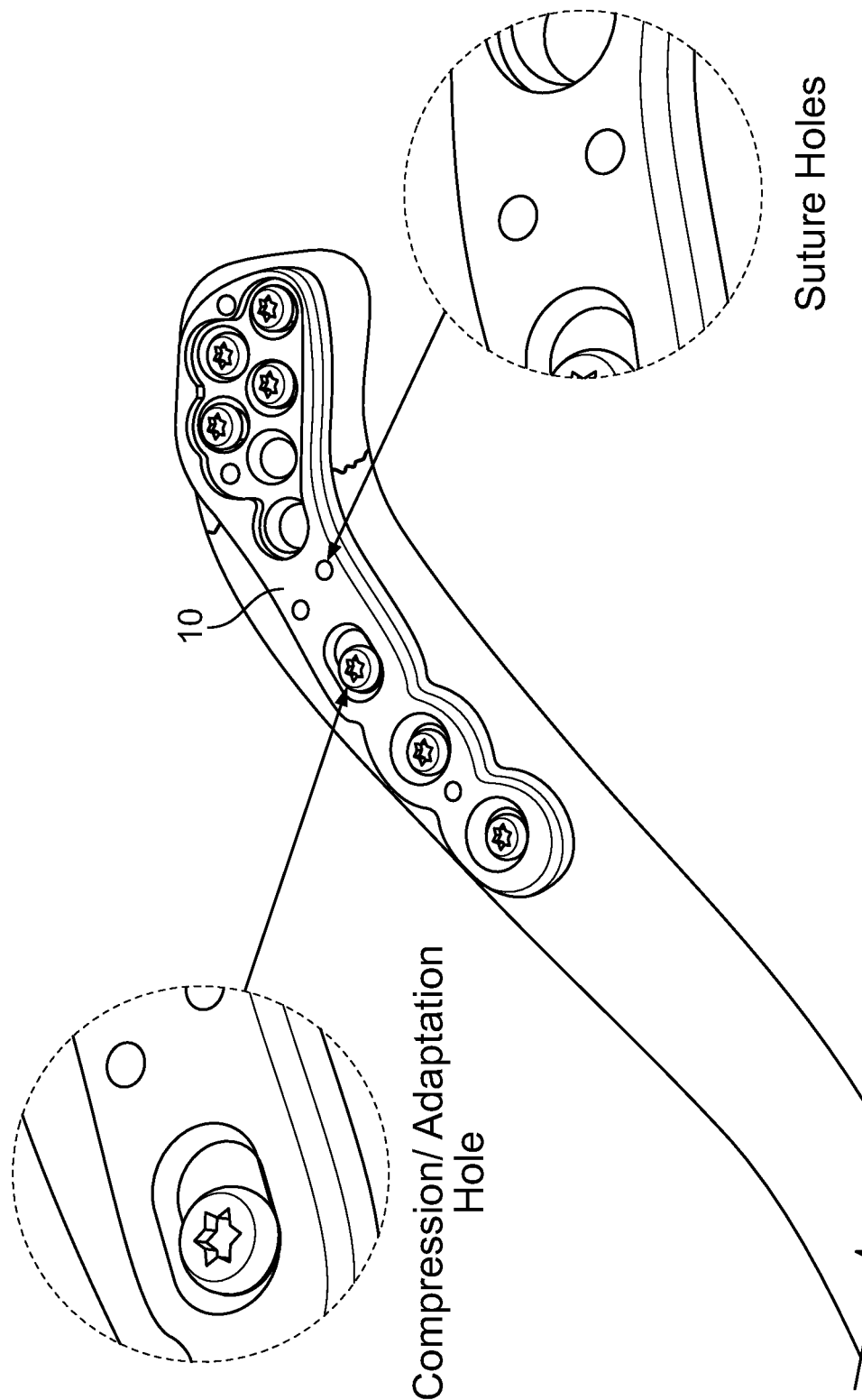
FIG. 10 is a perspective view of the bone plate of FIG. 1 shown fully attached to a fractured clavicle.

Remaining FIGS. 8-10 depict proper placement of plate 10 on a fractured clavicle. Specifically, as is shown in FIG. 8, plate 10 is first placed over a fracture site on the clavicle, so that the fracture line is spanned by at least a portion of the plate. This initial placement may be aided through the use of K-wires or sutures which can be received in holes 20 of plate 10. With the plate in this position, the above-discussed cooperation among plate 10, aiming block 30, and joystick 40 can be established. Any K-wires utilized may also be received within hole 34 of aiming block 30. Thereafter, fixation elements (represented by cylindrical elements 50 in FIG. 9) can be inserted through holes 32 of aiming block 30 and ultimately through holes 18 of plate 10. As is noted above, the additional structure provided by aiming block 30, and more particularly the extension provided by holes 32, allows for a more specific placement of screws at a given angle. In addition, it is noted that aiming block 30 may be utilized to guide a drill, which may be necessary to use prior to inserting screws. Additionally, remaining holes 12 and 14 of plate 10 may accept other screws for fixing plate 10 along the clavicle bone.

A fully fixed plate 10 with screws placed through certain of its holes is shown in FIG. 10. Again, although shown and discussed as being for use in connection with repairing a clavicle fracture, plate 10, aiming block 30, and joystick 40 may be configured to be utilized in repairing fractures of any bone within the human body. Likewise, it is noted that although specific constructions are shown in the figures, each component of the present invention may vary depending upon intended use or for aesthetic purposes.

Although the invention(s) herein has been described with reference to particular embodiments, it is to be understood that these embodiments are merely illustrative of the principles and applications of the present invention(s). It is therefore to be understood that numerous modifications may be made to the illustrative embodiments and that other arrangements may be devised without departing from the spirit and scope of the present invention(s) as defined by the appended claims.

It will also be appreciated that the various dependent claims and the features set forth therein can be combined in different ways than presented in the initial claims. It will also be appreciated that the features described in connection with individual embodiments may be shared with others of the described embodiments.

The invention claimed is:

1. A bone-fixation system comprising:
a bone plate having a section with a plurality of holes and a recessed area at least partially surrounding one or more of the holes, the recessed area defining a floor surface situated below a top surface of the plate and a peripheral wall surface arranged at an angle relative to the floor surface, wherein the floor surface extends at least partially between some or all of the plurality of holes; and
an aiming device having a body with a plurality of holes arranged to align with the plurality of holes in the plate and an extension, the extension being receivable within the recessed area and defining a bottom surface adapted to at least partially rest on the floor surface, wherein the extension includes a perimeter surface arranged at an angle relative to its bottom surface, the perimeter surface being sized and shaped to lie closely adjacent to the peripheral surface of the recessed area so that, when the extension is received in the recessed area, the aiming device is substantially non-movable relative to the bone plate in all directions except a removal direction extending away from the floor surface, the extension of the body being offset from a remainder of the body to define a step.

2. The bone-fixation system of claim 1, wherein when the extension of the aiming device is situated within the recessed area of the plate, each of the plurality of holes of the aiming device is aligned with a corresponding one of the plurality of holes of the plate.

3. The bone-fixation system of claim 1, wherein at least one of the plurality of holes of the aiming device is angled so as to direct a fixation member through a corresponding one of the plurality of holes of the plate and into bone at an angle.

4. The bone-fixation system of claim 1, wherein the bone plate includes a head, and the recessed area occupies a major portion of the head.

5. The bone-fixation system of claim 1, wherein the aiming device and the bone plate each include at least one hole adapted to receive a K-wire, the at least one hole of the aiming device aligning with the at least one hole of the plate when the aiming device is situated within the recessed area.

6. The bone-fixation system of claim 1, wherein the floor surface of the recessed area extends between each of the plurality of holes of the plate.

7. The bone-fixation system of claim 1 further comprising an insertion tool having a threaded portion, wherein the aiming device includes at least one threaded hole adapted to engage with the threaded portion of the insertion tool for manipulating the aiming device into engagement with the plate.

8. The bone-fixation system of claim 1, wherein a first and second of the plurality of holes of the aiming device are arranged so that fixation members inserted into the holes diverge.

9. The bone-fixation system of claim 1, wherein the peripheral wall surface defines a shape of the recessed area and the perimeter surface defines a shape of the extension, the shape defined by the perimeter surface being substantially the same as the shape defined by the peripheral wall surface.

10. A bone-fixation system comprising:
a bone plate having a section with a plurality of holes and a recessed area at least partially surrounding one or more of the holes, the recessed area defining a floor surface situated below a top surface of the plate, the floor surface extending at least partially between some or all of the plurality of holes;
an aiming device having a body with a plurality of holes arranged to align with the plurality of holes in the plate and an extension, the extension being receivable within the recessed area and defining a bottom surface adapted to at least partially rest on the floor surface; and
an insertion tool including a handle and a shaft, a distal end of the insertion tool being lockingly engageable with the aiming device so that the aiming device and insertion tool are manipulatable as a unit apart from the bone plate to place the aiming device into engagement with the plate.

11. The bone-fixation system of claim 10, wherein the aiming device includes at least one hole adapted to engage with the distal end of the insertion tool.

12. The bone-fixation system of claim 11, wherein the at least one hole is threaded, and the distal end of the insertion tool is threaded, such that the threaded end of the insertion tool is engageable with the at least one threaded hole in the aiming device.

13. The bone-fixation system of claim 10, wherein the insertion tool includes an extension projecting from the shaft and a shoulder, a diameter of the shoulder being greater than a diameter of the extension, the extension being insertable through at least one of the holes of the aiming device and into a hole in the plate so that the shoulder abuts a top surface of the aiming device.

14. The bone-fixation system of claim 13, wherein the distal end of the insertion tool is engageable with the plate and, once so engaged, the shoulder of the insertion tool contacts the top surface of the aiming device so as to compress the aiming device against the plate.

15. The bone-fixation system of claim 10, wherein the distal end of the insertion tool is engageable with the plate.

16. The bone-fixation system of claim 10, wherein the recessed area defines a peripheral wall surface arranged at an angle relative to its floor surface and the extension defines a perimeter surface arranged at an angle relative to its bottom surface, the perimeter surface being sized and shaped to lie closely adjacent the peripheral surface of the recessed area so that, when the extension is received in the recessed area, the aiming device is substantially non-movable relative to the bone plate in all directions except a removal direction extending away from the floor surface, the extension of the body being offset from a remainder of the body to define a step.

17. The bone-fixation system of claim 16, wherein the peripheral wall surface defines a shape of the recessed area and the perimeter surface defines a shape of the extension, the shape defined by the perimeter surface being substantially the same as the shape defined by the peripheral wall surface.

18. A bone-fixation system comprising:
a bone plate having a section with a plurality of holes and a recessed area at least partially surrounding one or more of the holes, the recessed area defining a floor surface situated below a top surface of the plate, the floor surface extending at least partially between some or all of the plurality of holes; and
an aiming device having a body with a plurality of holes arranged to align with the plurality of holes in the plate and an extension, the extension being receivable within the recessed area and defining a bottom surface adapted to at least partially rest on the floor surface, wherein the recessed area and the extension are sized and shaped such that, when the extension is received in the recessed area, each of the plurality of holes of the aiming device self-aligns with a corresponding one of the plurality of holes of the bone plate, the extension of the body being offset from a remainder of the body to define a step.

19. The bone-fixation system of claim 18, wherein the recessed area defines a peripheral wall surface arranged at an angle relative to its floor surface and the extension defines a perimeter surface arranged at an angle relative to its bottom surface, the perimeter surface being sized and shaped to lie closely adjacent to the peripheral surface of the recessed area so that, when the extension is received in the recessed area, the aiming device is substantially non-movable relative to the bone plate in all directions except a removal direction extending away from the floor surface.

20. The bone-fixation system of claim 19, wherein the peripheral wall surface defines a shape of the recessed area and the perimeter surface defines a shape of the extension, the shape defined by the perimeter surface being substantially the same as the shape defined by the peripheral wall surface.

21. The bone-fixation system of claim 18, wherein at least one of the plurality of holes of the aiming device is angled so as to direct a fixation member through a corresponding one of the plurality of holes of the plate and into bone at an angle.

22. The bone-fixation system of claim 18 further comprising an insertion tool having an engagement portion, wherein the aiming device includes at least one hole with an engagement portion adapted to lockingly interact with the engagement portion of the insertion tool so that the insertion tool and aiming device are manipulatable as a unit.

* * * * *